United States Patent [19]

Spears et al.

[11] Patent Number: 5,263,951
[45] Date of Patent: Nov. 23, 1993

[54] CORRECTION OF THE OPTICAL FOCUSING SYSTEM OF THE EYE USING LASER THERMAL KERATOPLASTY

[75] Inventors: Kenneth G. Spears, Skokie; Gerald Horn, Golf, both of Ill.

[73] Assignee: Kerus Medical Systems, San Francisco, Calif.

[21] Appl. No.: 512,023

[22] Filed: Apr. 16, 1990

Related U.S. Application Data

[63] Continuation-in-part of Ser. No. 342,202, Apr. 21, 1989, abandoned.

[51] Int. Cl.$^5$ .............................................. A61N 5/06
[52] U.S. Cl. ........................................ 606/12; 606/3; 606/5; 606/10; 606/13; 606/16; 606/17
[58] Field of Search ....................... 606/3-6, 606/10-13, 16, 17, 27, 28, 33; 128/362, 395, 397-400, 897, 898

[56] References Cited

U.S. PATENT DOCUMENTS

| | | | |
|---|---|---|---|
| 3,776,230 | 12/1973 | Neefe | 604/20 |
| 3,982,201 | 9/1976 | Rosenkrantz et al. | 372/75 |
| 4,461,294 | 7/1984 | Baron | 606/5 |
| 4,729,372 | 3/1988 | L'Gsperance, Jr. | 606/5 |
| 4,785,459 | 11/1988 | Baer | 372/75 |
| 4,838,266 | 6/1989 | Kozcol et al. | 606/5 |

FOREIGN PATENT DOCUMENTS

| | | | |
|---|---|---|---|
| 214712 | 3/1987 | European Pat. Off. | 128/303.1 |
| 831119 | 5/1981 | U.S.S.R. | 128/303.1 |

OTHER PUBLICATIONS

"A New Refractive Method For Laser Thermal Keratoplasty With The Co:MgF$_2$ Laser", G. Horn et al., presented at 2nd American-International Congress on Cataract, IOL and Refractive Surgery, ASCRS, Washington, DC, Apr. 25, 1989.

"Soviet Laser Is Used To Correct Hyperopia", Laura B. Bruck, Opthamology Times, Sep. 15, 1988.

"The Fyodorov Technique of Hyperopia Correction By Thermal Coagulation: A Preliminary Report", Andrew I. Caster, Jour. of Refractive Surgery, vol. 4, No. 3, May/Jun. 1988, pp. 105-108.

"A Classification of Refractive Corneal Surgery: Making Sense of Keratospeak", Archives of Ophthalmology, vol. 103, Oct. 1985, G. O. Waring III, pp. 21-27.

"Laser Interactions With The Cornea", J. M. Krauss et al., Survey of Ophthalmology, vol. 31:1, Jul./Aug. 1986, pp. 37-53.

"Corneal Topographic Changes After Radial Keratotomy", P. J. McDonnell et al., Ophthalmology, Jan. 1989, vol. 96:1, pp. 45-49.

"Preliminary Report of Los Alamos Keratoplasty Techniques", J. J. Rowsey et al., Ophthalmology, Aug. 1981, vol. 88:8, pp. 755-760.

"Infrared Laser Surgery of The Cornea", D. Stern et al., Ophthalmology, Oct. 1988, vol. 95:10, pp. 1434-1441.

"Modification of Rabbit Corneal Curvature With Change of Carbon Dioxide Laser Burns", Ophthalmic Surgery, W. A. Peyman et al., May 1980, vol. 11, pp. 325-329.

"Photorefractive Keratectomy: A Technique For Laser Refractive Surgery", C. R. Munnerlyn et al., J. Cataract Refract Surg., vol. 14, Jan. 1988, pp. 46-52.

"Ocular Use of The New Lasers", Ocular Surgery News, Mar. 1, 1989, pp. 34-44.

"Thermokeratoplasty (TKP) Temperature Profile", E. L. Shaw et al., Investigative Ophthalmology, Mar. 1974, pp. 181-186.

"Increase In Rabbit Corneal Curvature By Heated Ring Application", Gruenberg et al., Annals of Ophthalmology, Jan. 1981, pp. 67-70.

(List continued on next page.)

Primary Examiner—David M. Shay
Attorney, Agent, or Firm—Kenneth D'Alesandro

[57] ABSTRACT

A laser system applies energy of the proper wavelength to the cornea of the eye and the stroma of the cornea is thereby heated and changes permanently, causing the shape of the cornea to change. Laser treatment patterns are disclosed for correcting nearsightedness, farsightedness and astigmatisms.

49 Claims, 6 Drawing Sheets

OTHER PUBLICATIONS

"Thermokeratoplasty", A. R. Gasset et al., Ophthalmology, vol. 77, Jul./Aug. 1973, pp. 441–454.

"Thermokeratoplasty In The Treatment of Keratoconus", A. R. Gasset et al., Amer. Jour. of Ophthalmology, vol. 79:2, Feb. 1975, pp. 226–232.

"Thermokeratoplasty", J. v. Aquavella, Ophthalmic Surgery, vol. 5:1, Spring 1974, pp. 39–47.

"Thermokeratoplasty for Keratoconus", R. H. Keates et al., Ophthalmic Surgery vol. 6:3, Fall 1975, pp. 89–92.

"Alterations in Corneal Morphology Following Thermokeratoplasty", J. V. Aquavella et al., Arch. Ophthalmol., vol. 94, Dec. 1976, pp. 2082–2085.

"Damage To Epithelial Basement Membrane By Thermokeratoplasty", J. A. Fogle et al. Amer. Jour. of Ophthalm., vol. 83:3, Mar. 1977, pp. 392–401.

"Ophthalmic Applications of Infrared Lasers—Thermal Considerations", M. A. Mainster, Invest. Ophthalmol., vol. 18:4, Apr. 1979, pp. 414–419.

"Advanced Techniques in Ophthalomic Microsurgery vol. II Corneal Surgery" by L. Grand; The C. V. Mosby Company, st. Louis, 1981, pp. 147–150.

"Laser Treatment for Carcinoma of the Bronchus" by Hetzel et al; Brit. Med. J. vol. 286 Jan. 1, 1983 pp. 12–16.

CORRECTION OF THE OPTICAL FOCUSING SYSTEM OF THE EYE USING LASER THERMAL KERATOPLASTY

This application is a continuation-in-part, of application Ser. No. 07/342,202, filed Apr. 21, 1989, now abandoned.

BACKGROUND OF THE INVENTION

The field of the invention is the correction of nearsightedness (myopia), farsightedness (hyperopia), and astigmatism by changing the shape of the cornea.

Refractive corneal surgery which alters the shape of the cornea can be performed using a number of techniques. Lamellar refractive keratoplasty involves the placement of material in, or on the cornea to change its shape. For example, a disk of cornea material from a donor is sutured to the anterior surface of the cornea, or a synthetic material is implanted within the corneal stroma. Keratotomy changes the shape of the cornea by making a pattern of incisions in the cornea's anterior surface. Keratectomy involves the removal of a piece of the cornea in order to change the contour of its anterior surface, and thermokeratoplasty involves the application of heat. The heat is applied in a pattern which brings about the desired change in corneal shape and the heat may be produced by a thermal probe, a laser, or a radio frequency current.

All of the above techniques for altering the shape of the cornea, except for the last one, thermokeratoplasty, involves physical penetration of the anterior layers of the cornea. A well known way of practicing keratotomy, for example, involves the making of a series of incisions in the cornea in a radial pattern at a depth ranging from 80% to 95% of the cornea thickness. These incisions may be made with cutting instruments or with lasers, and they create lines of weakness around the periphery of the cornea which cause slight peripheral bulging and consequent central flattening of the cornea. This slight central flattening decreases the focusing power of the optic system to provide the desired correction for myopia. Keratotomy has the disadvantages associated with surgical incisions into the cornea, including risk of infection, risk of perforation of the cornea, loss of the eye, double vision and glare. In addition, there is difficulty in accurately controlling the amount of correction in the focusing power.

Keratectomy also involves cutting into the cornea and removing or ablating sections thereof to alter its shape. For example, an excimer laser may be used to sculpt the central region of the cornea to alter its curvature. This sculpting process involves the application of laser energy to the anterior surface of the cornea which ablates the cornea to the desired depth. To correct for 6 diopters of myopia, for example, an approximately 50 micron thickness must be removed from the anterior surface of the cornea in the corneal center. The major difficulty with this procedure is the removal of the anterior layers of the cornea, including the epithelium, basal membrane and Bowman's membrane. This can result in infection, recurrent erosion of the epithelium, and scarring of the corneal stroma and replacement of some of the ablated tissue with collagen that is less regular and less clear.

Thermokeratoplasty seeks to deliver heat to the underlying corneal stroma and it has been recognized heretofore that when heat is applied to the corneal stroma the shape, or contour, of the cornea will change. However, the problem has been to deliver a proper amount of thermal energy to the corneal stroma without damaging the anterior surface of the cornea and without damaging the delicate endothelium, the most posterior layer of the cornea. While efforts have been made and proposals have been made to use lasers for thermokeratoplasty, none have been particularly successful and none have been tried to correct myopia. Instead, the preferred techniques at the present time include the use of an electrically heated probe which is inserted through the anterior surface of the cornea and into the corneal stroma (i.e. penetrating thermokeratoplasty), or the application of radio frequency probes to the surface of the cornea which induces heating in the cornea.

SUMMARY OF THE INVENTION

The present invention relates to a system for changing the shape of the cornea by the heating of the corneal stroma with a laser of proper wavelength and power. More particularly, the present invention includes: means for generating a laser beam which has a wavelength such that the laser beam's absorption coefficient when passing through water ranges from 5 cm$^{-1}$ to 114 cm$^{-1}$; means for receiving and directing the laser beam onto the cornea such as a probe which connects to receive the laser beam and which engages the cornea of the patient and directs the laser beam onto the cornea; means for shaping the laser beam into a treatment pattern; means for controlling the amount of heating in the corneal stroma by the laser beam; means for producing light energy; means connected to the probe for directing such light energy to the cornea and gathering light energy which is scattered by corneal haze; and a detector connected to receive the gathered light energy and being operable to produce a signal indicative of the amount of heating in the corneal stroma.

A general object of the invention is to provide a system for changing the shape of the cornea without penetrating or damaging the anterior surface of the cornea. By applying laser energy at the desired wavelength, the corneal stroma is heated without unduly heating the anterior or posterior corneal surfaces or membranes. By controlling the energy density and duration of the laser, permanent changes in the corneal stroma can be achieved with a consequent permanent change in the shape of the cornea.

Another general object of the invention is to provide a nonpenetrating system for correcting myopia using thermokeratoplasty. Both radial and disc shaped treatment patterns have been found to reduce the curvature of the cornea, and hence, correct for myopia. The amount of correction can be precisely controlled by the selection of the treatment pattern and control of the applied laser energy.

Another object of the invention is to provide a system for changing the shape of the cornea which is easy to use. The probe includes a collar which has an annular shaped end that firmly engages the surface of the patient's cornea. A fiber optic connection is made between the laser and this collar and the laser beam is precisely aligned to enter the cornea at the desired locations within the ring defined by the engaging annular collar. The collar reduces eye movement, and to the extent there is any movement, the laser beam moves with the collar and eye to maintain its alignment on the cornea.

The collar can be easily changed to alter the shape or size of the treatment pattern.

A more specific objective of the invention is to change the shape of the cornea without producing the risks and problems associated with incisions, penetrations or ablation of the anterior surface of the cornea. By controlling the wavelength of the laser, its energy density and its treatment duration, the desired change in shape is achieved without appreciable effect on the epithelium, basal membrane or Bowman's membrane, or endothelium of the cornea.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

GENERAL DESCRIPTION OF THE INVENTION

Figure 1:
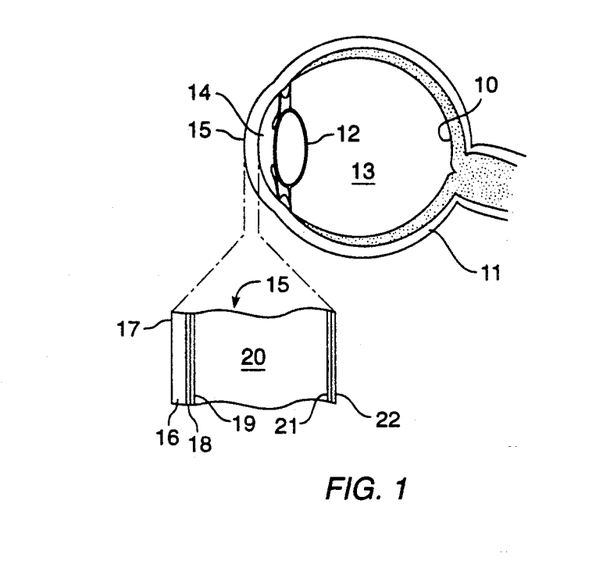
FIG. 1 is a view in cross section of the human eye, with a magnified cross section of a portion of the cornea.

Referring particularly to FIG. 1, the human eye is a system of lenses which focus light on a retina 10 located to the rear of a substantially spherical body defined by a sclera 11. These include a lens 12 which separates the vitreous body 13 from an anterior chamber 14, and the cornea 15 which defines the forward wall of the anterior chamber 14. The cornea 15 is a smoothly curved, clear structure which has a smaller radius of curvature than the opaque sclera 11 and which bulges slightly from the smooth outer contour of the eye.

Refractive errors occur when these lenses do not focus the incoming light on the retina. In such case, an additional corrective lens such as glasses or contact lenses may be added to provide clear vision. In the alternative, the corneal curvature of the eye may be changed to make the proper correction in focal power. Such changes in focal power are measured in increments called diopters.

The present invention is a system for changing the focal power of the eye lenses by altering the shape, or curvature, of the cornea 15. Referring still to FIG. 1, the cornea 15 is comprised of a number of distinct layers of tissue which together have a thickness ranging from 520 to 650 microns at the center and 600 to 1,000 microns at the periphery. These include an epithelium 16 which presents a very smooth and clear outer surface 17 which is exposed to the surrounding environment and which has a thickness of from 50 to 100 microns. Immediately behind the epithelium 16 are two very thin layers, a basal membrane 18 and Bowman's membrane 19 which together may be from 10 to 17 microns thick. Many documented complications can be avoided by not disturbing these three outer layers of the cornea 15 when implementing any corrective strategy.

The main body of the cornea is comprised of a thick layer called the corneal stroma 20 which comprises up to 90% of the cornea's thickness. The corneal stroma is comprised of cells and tape-like bands of fibers called lamellae. For the purpose of the present invention, it is important to note that 75% of the corneal stroma is comprised of water.

Located behind the corneal stroma are two thin layers, Descemet's membrane 21 and the endothelium 22. Descemet's membrane 21 grows to a thickness of about 7 microns and the endothelium is a single layer of cells having a thickness of about 5 microns.

The cornea 15 is the eye's first and strongest refracting surface (43 diopters). Several conditions, including myopia, hyperopia and astigmatism result in improper image formation on the retina 10, and while these conditions may not be caused by the cornea 15, all three can be corrected by reshaping the cornea 15.

The present invention produces an amount of heating of the outer surface 17 of the cornea 15 and the outer three layers 16, 18 and 19 of the cornea below a level which could possibly cause permanent damage thereof. This heating level is accomplished by using a laser which has an appropriately absorbing wavelength. As a very general proposition, laser energy produced by lasers with very short wavelengths (for example, argon (0.514), Nd:YAG (1.06, 1.32) lasers) is not absorbed sufficiently by the cornea 15 and passes through the cornea 15 to be absorbed by other structures in the eye. On the other hand, laser energy produced by lasers with very long wavelengths (for example, $CO_2$ (10.6), HF (2.9), Erbium (2.83) lasers) is highly absorbed by the outer layers of the cornea 15 and the desired heating effect does not reach the corneal stroma 20 without overheating the outer layers 16, 18 or 19.

Figure 2:
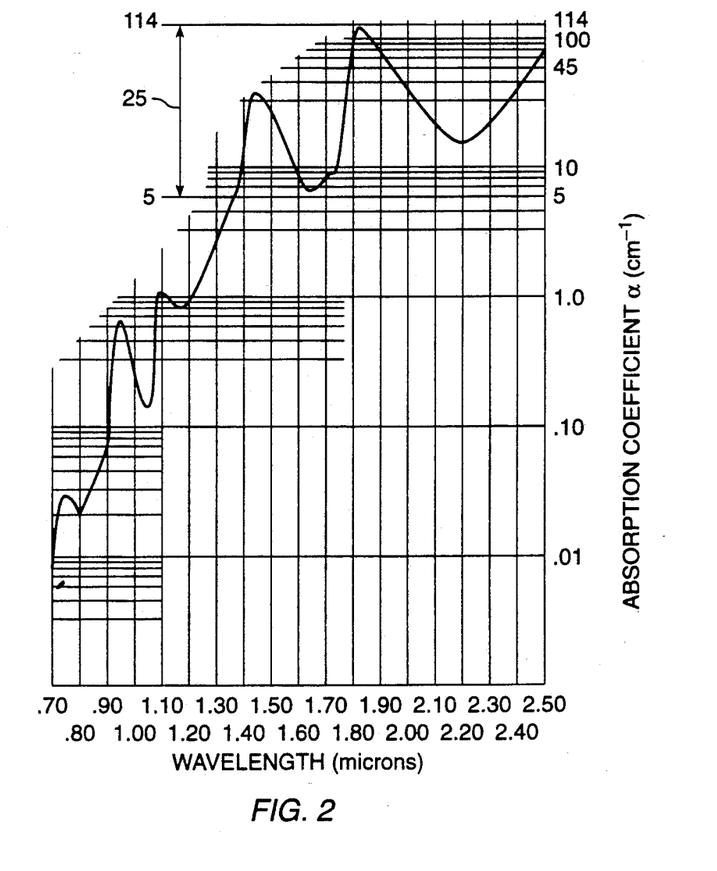
FIG. 2 is a graphic representation of the absorption characteristics of water.

As illustrated by the absorption graph in FIG. 2, however, the relationship between laser wavelength and depth of heating is far from linear. The graph in FIG. 2 is a plot of the absorption coefficient of water ($\alpha$) as a function of laser wavelength in microns (micrometers).

It is readily apparent that although the general rule that increased wavelength results in greater absorption holds true, within selected ranges of the entire spectrum the curve is very nonlinear and is even contrary to the general rule. It is a teaching of the present invention that an important factor in obtaining proper heating of the corneal stroma is the selection of a wavelength for the laser which provides the desired absorption coefficient. Absorption coefficients as referred to herein are defined in terms of the exponential attenuation of the incident intensity of the laser beam and are expressed in $cm^{-1}$. More specifically, absorption coefficients ($\alpha$) for water which are within the range of 5 $cm^{-1}$ to 114 $cm^{-1}$ have been found to be usable for proper heating of the corneal stroma. This usable range of absorption coefficients is indicated by the arrows 25 in FIG. 2. Furthermore, it is believed that the benefits are maximum in a range of about 5 $cm^{-1}$ to 45 $cm^{-1}$. As the absorption curve in FIG. 2 indicates, for example, laser wavelengths of 1.38 microns to 2.50 microns (and up to 2.70 microns, by extrapolation of the illustrated curve in FIG. 2) have absorption coefficients that are included within the usable range.

Figure 3:
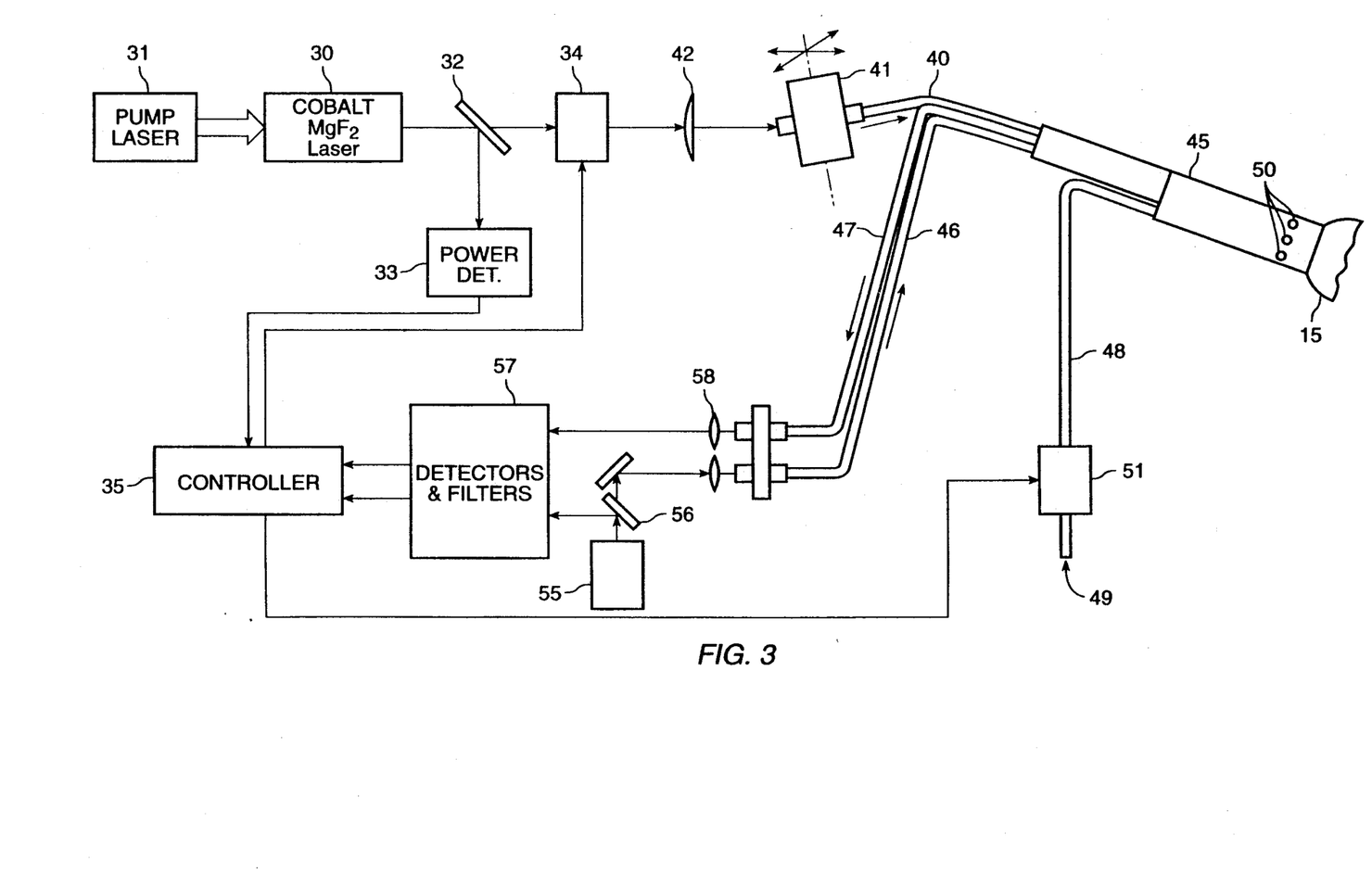
FIG. 3 is a pictorial representation of the preferred embodiment of the treatment system of the present invention.

Referring particularly to FIG. 3, the system of the present invention includes a number of elements for producing and controlling the delivery of laser energy to the corneal stroma. The heart of the system is a $Co:M_gF_2$ solid-state laser 30 which is broadly tunable to a wavelength within the range of 1.55 microns to 2.25 microns. The laser 30 is pumped by a continuous wave, 1.32 micron Nd:YAG laser 31, and it produces a continuous average output of from 0.5 to 2.0 watts at the indicated range of wavelengths. Construction of the laser 30 is described in an article by Peter F. Moulton "An Investigation of the $Co:M_gF_2$ Laser System", in IEEE Journal of Quantum Electronics, Vol. QE-21, No. 10, October 1985. The output of the laser 30 is directed at a beamsplitter 32 which directs a fixed proportion of its energy to a power detector 33 and allows the remainder of the energy to pass through to an electronically operable shutter 34. This power detector 33 provides a signal which indicates the level of the laser energy delivered to the shutter 34 and this power signal is input to a controller 35. The electronic shutter 34 is controlled by an output on the controller 35 to interrupt the laser beam and thereby control the pulse duration, pulse rate, and duty cycle of the delivered laser energy.

The controlled laser energy is delivered to the cornea 15 by an optical fiber 40. The input end of the optical fiber 40 extends through a tiltable mount 41, and the laser energy is focused on this end by a convex lens 42. The tiltable mount 41 holds the end of the optical fiber 40 stationary, but it enables the longitudinal axis of the fiber 40 to be tilted with respect to the longitudinal axis of the laser beam emanating from the lens 42. As will be explained below, the adjustment of this tilt angle enables the energy density of the laser beam to be contoured such that less energy is delivered at its center than its periphery.

The other end of the optical fiber 40 connects to a probe assembly 45 which engages the cornea 15 and is held in fixed relation thereto. The probe assembly 45 has a number of configurations which will be described in more detail below, but the preferred embodiment also includes connections to two additional optical fibers 46 and 47 and to a hose 48. The hose 48 delivers a stream of cooling gas such as Freon, which is input at 49 and flows into the probe assembly 45 where it cools the surface of the cornea 15 being treated. The cooling gas exits through openings 50 around the periphery of the probe assembly 45, and the flow of cooling gas is controlled by an electric gas valve 51 which connects to an output on the controller 35.

The optical fibers 46 and 47 provide treatment feedback information when the system is operated in a closed loop mode. More particularly, the optical fiber 46 delivers light produced by a light source 55 to the cornea 15 in order to determine the degree of stromal haze which has been produced by the laser heat treatment. The light 55 is either a laser (for example, He-Ne) or a conventional light source with a filter which produces light having a wavelength in the range of 0.4 microns to 2.2 microns. This light is scattered by the stromal haze and is delivered back by the other optical fiber 47. The degree of treatment is determined by measuring the strength of the scattered light relative to the strength of the light source 55. A beam splitter 56 reflects a fixed portion of the light from source 55 to a photo detector and filter circuit 57 and the scattered light from fiber optic 47 is also applied to the circuit 57 through a convex lens 58. The magnitudes of the reference light source signal and the scattered light signal are compared by the controller 35 to determine when the stromal haze has reached a level that indicates treatment is to be stopped. When this occurs, the controller 35 closes the electronic shutter 34 and provides a visual signal to the system operator.

In an alternative embodiment of the invention, the light source 55 produces light energy at two distinct wavelengths (for example, 0.4 microns and 0.6 to 0.82 microns). Two beams are used in order to offset the signal component in the returned light which is due to reflection off the surface of the cornea rather than scattering from within the cornea. Both light beams reflect equally off the cornea's surface, but because of their different wavelengths, they are scattered differently. Thus, as the amount of treatment increases, the amount of scattering increases differently and this difference signal can be used to measure the degree of treatment. To achieve this measurement, the light which is returned through optical fiber 47 is broken down into its two components and the relative strengths of these components are measured by the detectors and filters circuit 57.

Figure 4:
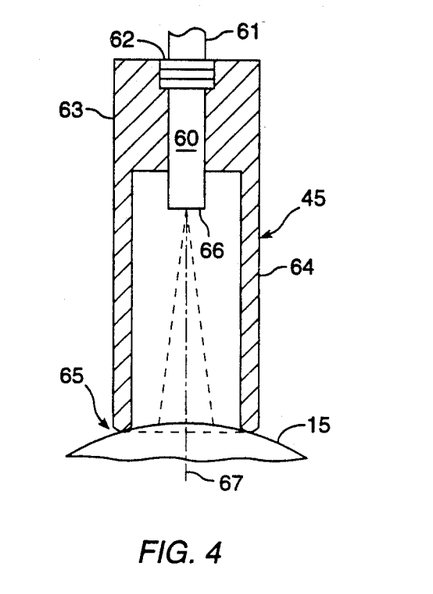
FIG. 4 is a view in cross section of the probe assembly which forms part of the system of FIG. 3.

Referring particularly to FIG. 4, a first preferred embodiment of the probe assembly 45 includes a circular cylindrical metal probe 60 which connects to the bundle 61 of optical fibers 40, 46 and 47 and the hose 48. A threaded flange 62 is machined around the probe 60 and it is received in a threaded opening formed on the enclosed end 63 of a circular cylindrical metal collar 64. The collar 64 presents an annular shaped forward end 65 that is smoothly rounded and suitable for engaging the surface of the cornea 15. The probe assembly 45 is retained in engagement with the cornea 15 using hand pressure, which is the technique commonly employed when using contact lenses in laser eye surgery. Using this technique, the probe assembly 45 remains aligned with the optical axis 67 of the eye despite small eye movements by the patient.

The laser energy is directed out the forward end 66 of the probe 60 and is coaxial with the optical axis of the eye 67. The laser energy is distributed in a substantially circular pattern and it diverges slightly as it travels away from the end of the probe 60. Indeed, the size of the circular laser pattern which impinges on the cornea 15 is determined by selecting a collar 64 of the appropriate length. That is, a set of collars 64 of varying lengths are provided and may be easily attached to the threaded probe 60. Each collar 64 provides a circular treatment pattern of calibrated size.

Figure 5:
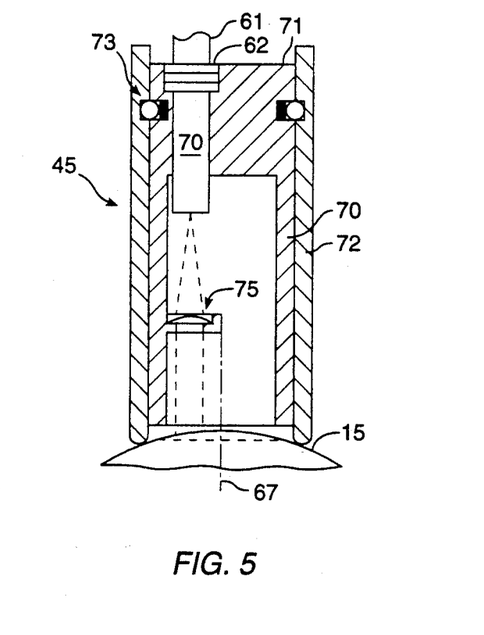
FIG. 5 is a view in cross section of an alternative probe assembly which can be used in the system of FIG. 3.

A second preferred embodiment of the probe assembly 45 is illustrated in FIG. 5. The collar in this embodiment is more complex and includes an inner collar 70 which receives the probe 60 in threaded engagement in an opening formed in its closed end 71. A circular cylindrical outer collar 72 extends around the inner collar 70 and it is attached thereto by a detent mechanism 73. The detent mechanism 73 prevents the collars 70 and 72 from sliding apart, but it enables the inner collar 70 to be rotated about the optical axis 67 while the lower end of the outer collar fixedly engages the cornea 15. The detent mechanism 73 defines eight discrete index positions and the inner collar 70 can be rotated into any of these.

The probe 60 in the embodiment of FIG. 5 is not mounted coaxial with the optical axis 67. Instead, it is offset radially to one side. Mounted directly beneath it is a cylindrical lens 75. The laser energy emanating from the lower end of the probe 60 is in a circular pattern and when it is scattered by the lens 75, its pattern is altered to form a single line which is directed radially outward from the optical axis 67. By rotating the inner collar 70, this radial line pattern can be oriented at selected locations around the optical axis 67 and by spacing the cylindrical lens 75 at different axial distances from the probe 60, different radial line lengths can be produced.

It should be apparent that many different collars can be provided for attachment to the probe 60 to produce a wide variety of laser treatment patterns. The probe 60, however, is the same in all configurations and is merely screwed into the collar of choice to form the probe assembly 45.

Figure 6A:
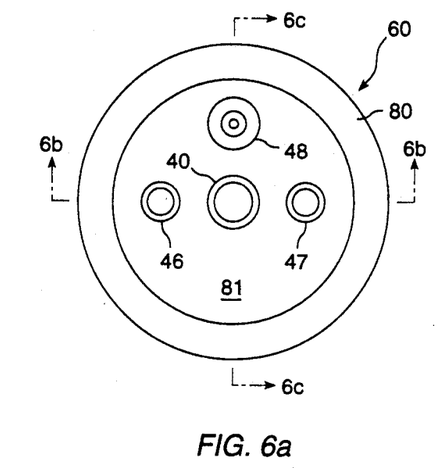
FIGS. 6A-6C are views in cross section of the probe which forms part of the assemblies of FIGS. 4 and 5.
Figure 6B:
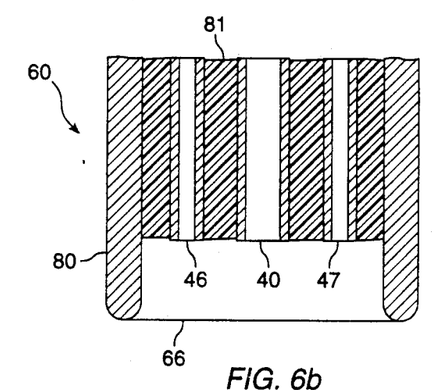
Figure 6C:
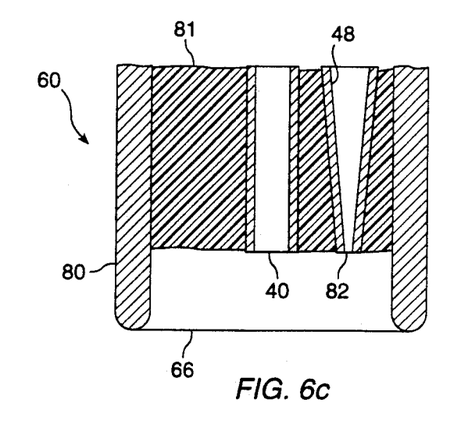

The construction of the probe 60 is shown in detail in FIGS. 6A-6C. The probe 60 is a metal sleeve 80 which receives the three optical fibers 40, 46 and 47 and the hose 48. These elements are fixed in the positions shown with an epoxy binder 81 which fills the voids and extends downward substantially level with the exposed ends of the optical fibers 40, 46 and 47 and the hose 48. As shown best in FIG. 6C, the end of the hose 48 is constricted to form a nozzle 82 that causes a pressure drop in the Freon gas flowing through it. This pressure drop lowers the temperature of the cooling gas.

It should be apparent to those skilled in the art that many alternative structures may be employed in the above described treatment system. For example, lasers which will produce the appropriate treatment wavelengths to provide the required absorption coefficients in water of between 5 cm$^{-1}$ and 114 cm$^{-1}$ are in the range of about 1.38 microns to about 2.70 microns and can be constructed using Holmium$^{+3}$ ions Thullium$^{+3}$ ions or Erbium$^{+3}$ ions or mixtures thereof in either a YAG, YSGG or YLF crystalline media. The laser 30 may also be a diode laser constructed to produce energy of the proper wavelength. Also, the laser 30 may be pumped by a diode laser of the proper wavelength as described in an article by Thomas M. Baer "Diode Laser Pumping of Solid-State Lasers" published in the June 1986 issue of *Laser Focus*.

There are many ways in which the treatment system of FIG. 3 may be used to correct vision. The particular method used will depend on the type of correction to be made (myopia, hyperopia, or astigmatic) and the degree of correction (diopters).

Figure 7:
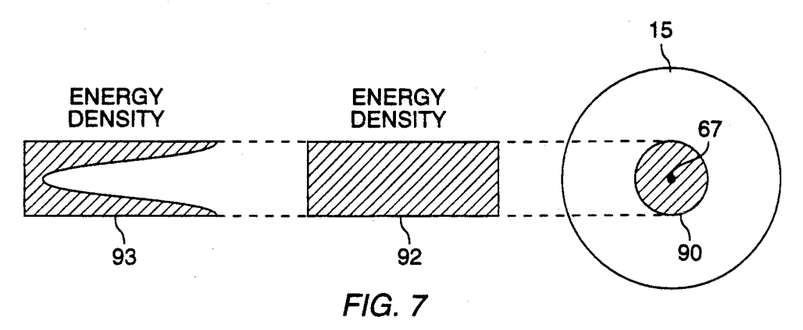
FIG. 7 is a pictorial view of a treatment pattern for correction of myopia using the system of FIG. 3.
Figure 8:
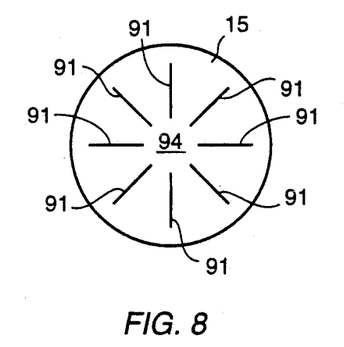
FIG. 8 is a pictorial view of another treatment pattern for myopia.

There are two treatment patterns which may be employed for myopic correction: a central disc 90 as shown in FIG. 7 and radial lines 91 as shown in FIG. 8. The central disc pattern 90 is coaxial with the optical axis of the eye and it may have a diameter from 2 millimeters to 7 millimeters, although a range of 3 to 5 millimeters is preferred. The laser may be applied at an average energy density of from 0.1 to 1.5 Joules/square millimeter. Average energy density is calculated by measuring the power (in Watts) applied to a nominal treated area of the cornea (in square millimeters) and multiplying this computed Watts/square millimeter value by a time factor that is the product of the laser treatment time and its duty cycle (i.e., the fraction of time that the laser is on) utilized in treating the cornea to achieve the desired degree of correction. The treatment causes the central region of the cornea to flatten and to thereby reduce its focal power.

While the energy distribution across the treatment disc 90 may be uniform as shown at 92, the preferred method is to contour the energy density profile as shown at 93 such that it is much reduced near the optical axis of the eye. This is accomplished, for example, by tilting the input of the fiber optic 40 with respect to the applied laser beam as described above with reference to FIG. 3. The greater the tilt, the lower the energy density at the center of the output beam. Table A is a chart containing example treatment parameters and the resulting corrections when a 3.0 millimeter central disc pattern 90 is employed.

TABLE A

| | Myopic Corrections Using Central Disc Pattern | | | | |
|---|---|---|---|---|---|
| CORRECTION (Diopters) | AVERAGE JOULES/mm$^2$ | TILT (Degrees) | TIME (Seconds) | DUTY CYCLE (%) | WAVELENGTHS (Microns) |
| 5.6 | 1.40 | 0° | 20 | 100 | 1.86 |
| 3.1 | 0.50 | 0° | 8.5 | 100 | 2.15 |
| 5.0 | 0.22 | 6° | 6.0 | 100 | 1.86 |

The radial line pattern 91 may also be employed to correct myopia. The treatment lines 91 are produced using the probe assembly of FIG. 5, and either 4, 6, 8 or 10 symmetric radial lines may be used. The energy density of the applied laser energy ranges from 0.1 to 1.5 Joules/mm$^2$ and each radial line 91 may have a length from 2 millimeters to 4 millimeters. The diameter of the untreated central region 94 of the cornea may range from 2.5 millimeters to 6.0 millimeters and the width of each radial treatment line 91 is from 0.5 millimeters to 1.5 millimeters. This treatment pattern causes the desired flattening of the cornea's untreated central region 94. Table B is a chart containing example treatment parameters and the resulting corrections when the radial pattern 91 having eight lines which are each 3.0 millimeters long and 1.0 millimeter wide is employed.

TABLE B

| | Myopic Corrections Using Radial Pattern | | | | |
|---|---|---|---|---|---|
| CORRECTION (Diopters) | AVERAGE JOULES/mm$^2$ | CENTRAL DIAMETER | TIME SECONDS | DUTY CYCLE (%) | WAVELENGTH (Microns) |
| 8.0 | 0.9 | 4.0 mm | 2.0 | 80 | 1.86 |
| 8.9 | 0.6 | 4.0 mm | 1.5 | 80 | 2.15 |

Figure 9:
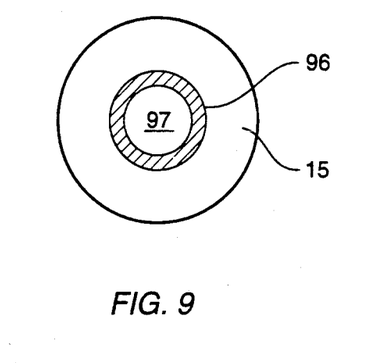
FIG. 9 is a pictorial view of a treatment pattern for the correction of hyperopia.

Referring particularly to FIG. 9, hyperopic correction is achieved with the present invention by producing an annular treatment pattern 96. This treatment pattern is produced by placing an axicon lens between the probe 60 and the cornea 15 or tilting the fiber to a large angle with respect to the incoming laser beam. The outer diameter of the annular pattern 96 may range from 4.5 millimeters to 9.0 millimeters and its width in the radial direction is from 10% to 20% of its outer diameter. An average laser beam energy density of form 0.1 to 1.5 Joules/mm$^2$ is employed to achieve the desired degree of correction.

The annular pattern 96 increases the curvature of the central untreated region 97 and thereby increases the focal power of the cornea 15. Table C is a chart containing example treatment parameters and the resulting corrections when the annular treatment pattern 96 is employed with a laser having a wavelength of 2.1 microns.

diffusion from the perimeter. Furthermore, it has been found that the specific laser pattern employed can be adjusted to create many different profiles of corneal curvature versus radial distance. Also by increasing the distance from the fiber to the cornea this pattern can be applied over larger areas.

TABLE D

| Myopic Corrections Using A Contoured Central Disc Pattern | | | | |
|---|---|---|---|---|
| Correction (Diopters) | Average Joules/mm$^2$ | Maximum Watts/mm$^2$ | Time (Seconds) | Wavelength (microns) |
| 2.2 | 0.16 | 0.053 | 4 | 2.06 |
| 3.6 | 0.20 | 0.033 | 8 | 2.06 |
| 3.5 | 0.22 | 0.036 | 8 | 2.00 |
| 6.6* | 0.21* | 0.034 | 8 | 2.00 |
| 3.0 | 0.20 | 0.033 | 8 | 1.97 |
| 3.2 | 0.20 | 0.033 | 8 | 1.94 |

*Denotes two successive treatments with a nominal delay of about 20 seconds.

TABLE C

| Hyperopic Corrections Using Annular Pattern | | | | | |
|---|---|---|---|---|---|
| CORRECTION (Diopters) | OUTER DIAMETER | AVERAGE JOULES/mm$^2$ | INNER DIAMETER | TIME (Seconds) | DUTY CYCLE (%) |
| 2.5 | 6 mm | 0.6 | 4 mm | 0.88 | 63 |
| 5.3 | 7 mm | 1.0 | 5 mm | 1.00 | 100 |

Figure 10:
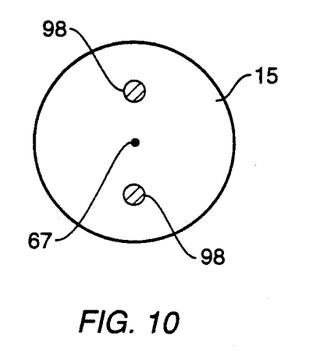
FIGS. 10 and 11 are pictorial views of alternative treatment patterns for correction of astigmatism.
Figure 11:
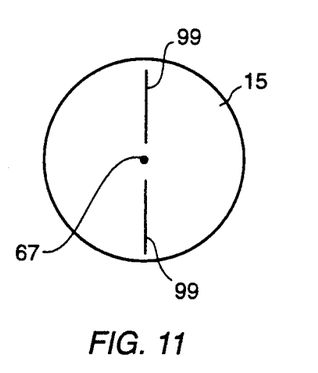

Many treatment patterns may be used to correct for astigmatism. The above described patterns perform their corrective functions by altering the cornea about the central optic axis. This is achieved by using treatment patterns which are symmetrical about the central optic axis in all directions. In contrast to such treatment patterns having 4 fold or greater rotational symmetry, astigmatic corrections are made with treatment patterns which have "2 fold symmetry". Two such patterns are shown in FIGS. 10 and 11 where the treatment zones are located symmetrically above and below the central optic axis 67, but none are located symmetrically to the left and right as in the pattern of FIG. 8. Such 2 fold symmetric treatment for astigmatism may employ circular patterns 98 as shown in FIG. 10, radial line patterns 99 as shown in FIG. 11, or any other shape which will provide similar changes in the cornea. The treatment parameters for the astigmatic patterns are similar to those discussed above.

Table D is a chart containing example treatment parameters and the resulting corrections when a contoured central disc pattern is employed. To achieve this laser pattern, a cylindrically symmetric absorbing filter was employed. The pattern has a relative power level as a function of radial distance which is measured by scanning the laser beam with a small aperture at the entrance of a power meter. Furthermore, additional power measurements were taken through a much larger hole of nearly a millimeter in order to provide a measure of peak power over a size that is significant for thermal heating effects on corneal structures. The laser pattern measured at the position of the cornea has 50% of the peak power at 2 mm radius, 90% at 1.6 mm radius, maximum power at 1.1 mm radius, and a central area of reduced power. The central area, when measured through an aperture of 0.042 inch diameter (1.067 mm), was 45% of the maximum power, which was measured with the same aperture centered at a 1.1 mm radius. The resulting contoured pattern has been found to provide nearly constant curvature changes in the corner for the central 2.5-3 mm diameter (measured with 0.5 mm increments). An effect of this reduction in power at the center of the pattern is believed to be a reduction in the likelihood of overheating the corneal center by thermal In regard to Table D it should be noted that the duty cycle for the data is 100% (i.e., a continuous laser). The average Joules/mm$^2$ is computed using 4.5 mm as the average diameter. The maximum Watts/mm$^2$ is measured using a 1.067 mm diameter aperture at a radius of 1.1 mm. The correction is an average over the center 3 mm. These treatments resulted in no visible haze in the cornea.

The data in Table D identifies a range of wavelengths which are usable to achieve correction of myopia. As depicted in FIG. 2, these wavelengths correlate to absorption coefficients in the range of about 45 cm$^{-1}$ to 114 cm$^{-1}$. In addition, the tabulated data demonstrates the effectiveness of employing multiple treatments to achieve corneal correction. The data demonstrates the increased correction in diopters achieved with the use of a second treatment over a relatively short time interval, for example, of about 10 seconds up to 3 hours. However, it is to be recognized that the present process for achieving corneal correction may be conducted employing time intervals of longer duration, for example, at least 4 days.

Furthermore, from the data in Table D and from other experiments conducted with rabbits, a generally preferred relationship between Watts/mm$^2$ and time of exposure has been determined for use in accomplishing corneal correction employing a continuous laser. Specifically, it is estimated that the upper time limit for continuous laser exposure is approximately calculated by dividing 0.575 by the maximum Watts/mm$^2$ in Table D and then subtracting 5.6 seconds. The maximum Watts/mm$^2$ in Table D were selected to provide 80-88% of the power that would be necessary to result in visible haze at the indicated times. A typical maximum was 0.0423 Watts/mm$^2$ at 8 seconds. Time shorter than about 2 seconds and longer than about 8 seconds would require adjustment to the formula. Repetitive pulsing of the laser to produce a similar integrated time profile of energy deposition in Joules/mm$^2$ would provide similar changes in corneal curvature. For example, if greater Watts/mm$^2$ are selected and the time intervals between pulses are adjusted to initially provide smaller intervals with progressively increasing intervals, then a temperature increase over time similar to that achieved by continuous laser heating would result that does not cause a corneal haze to form. Such pulsing profiles may be used to provide control of corneal heating that is more flexible than achieved with continuous heating; for example, this method can be used for holding a narrow range of maximum temperatures over a variable time.

We claim:

1. A system for changing the shape of the cornea of an eye by heating a corneal stroma to correct vision, the combination comprising:

means for generating a laser beam which has a wavelength such that the laser beam's absorption coefficient when passing through water ranges from 5 cm$^{-1}$ to 114 cm$^{-1}$;

means for directing the laser beam onto the cornea, said means being a probe assembly which connects to receive the laser beam and which engages the cornea of a patient;

means for shaping the laser beam into a treatment pattern; and means for controlling the amount of heating in the corneal stroma in a manner such that said laser beam having said wavelength with said adsorption coefficient and shaped into said treatment pattern is directed onto the cornea for a period of time of about one second or more to thereby control the change in shape of the cornea without incising, coagulating, scarring or ablating the corneal stroma; and an optical fiber having one end positioned in the laser beam and its other end connected to the probe assembly, and the longitudinal axis of the optical fiber at its one end tilted with respect to the direction of the laser beam.

2. The system as recited in claim 1 which includes means for controlling the amount of tilt to thereby enable the treatment pattern energy density to be controllably contoured.

3. A system for changing the shape of the cornea of an eye by heating a corneal stroma to correct vision, the combination comprising:

means for generating a laser beam which has a wavelength such that the laser beam's adsorption coefficient when passing through water ranges from 5 cm$^{-1}$ to 114 cm$^{-1}$;

means for directing the laser beam into the cornea, said means being a probe assembly which connects to receive the laser beam and which engages the cornea of a patient;

means for shaping the laser beam into a treatment pattern;

means for controlling the amount of heating in the corneal stroma in a manner such that said laser beam having said wavelength with said adsorption coefficient and shaped into said treatment pattern is directed onto the cornea for a period of time of about one second or more to thereby control the change in shape of the cornea without incising, coagulating scarring or ablating the corneal stroma;

means for producing light energy;

means connected to the probe assembly for directing the light energy to the cornea and gathering light energy which is scattered by corneal haze; and detector means connected to receive the gathered light energy and being operable to produce a signal indicative of the amount of heating in the corneal stroma.

4. The system as recited in claim 3 in which the means for shaping the laser beam into a treatment pattern produces a pattern having 2 fold rotational symmetry about the center region of the cornea and which causes the cornea to change shape in such manner as to correct astigmatism.

5. The system as recited in claim 3 in which the means for producing light energy produces light at two separate wavelengths and the detector means produces the signal indicative of the amount of heating by comparing the relative amounts of gathered light energy at the two separate wavelengths.

6. The system as recited in claim 3 in which the means for generating the laser beam includes a diode laser.

7. The system as recited in claim 3 in which said laser beam has a wavelength in the range of 1.38 microns to 2.70 microns.

8. The system as recited in claim 3 in which said absorption coefficient of said laser beam when passing through water ranges from 5 cm$^{-1}$ to 45 cm$^{-1}$.

9. The system as recited in claim 3 in which said controlling means is adapted for delivery of laser energy to the cornea in multiple treatments over short time intervals.

10. The system as recited in claim 3 in which said controlling means is adapted for delivery of laser energy to the cornea continuously.

11. The system as recited in claim 3 in which said controlling means is adapted for delivery of laser energy to the cornea by pulsing or modulating the energy input.

12. The system as recited in claim 1 wherein said laser beam is directed onto the cornea along the visual axis of the eye.

13. The system as recited in claim 3 wherein said laser beam is directed onto the cornea along the visual axis of the eye.

14. The system as recited in claim 3 in which the means for shaping the laser beam into a treatment pattern produces at least one line which is directed radially outward from the center of the cornea and the treatment pattern is a series of such radial lines which are disposed around an untreated central region and which cause the untreated central region to flatten such that its focal power is reduced.

15. The system as recited in claim 14 in which the diameter of the untreated central region is from 2.5 to 6.0 millimeters and each radial treatment line has a length of 2.0 to 4.0 millimeters.

16. The system as recited in claim 14 in which the treatment pattern includes from four to eight radial treatment lines which are spaced equidistantly about the untreated central region.

17. The system as recited in claim 3 in which the means for shaping the laser beam into a treatment pattern produces an annular pattern which encircles the central region of the cornea and which causes the curvature of the central region of the cornea to increase such that its focal power is increased.

18. The system as recited in claim 17 in which the outer diameter of the annular treatment pattern is from 4.5 to 9.0 millimeters.

19. The system as recited in claim 3 in which the means for generating the laser beam includes a laser medium containing $Co^{2+}$ ions in an $M_gF_2$ crystalline media.

20. The system as recited in claim 19 in which the laser medium is pumped by a diode laser.

21. The system as recited in claim 16 in which the means for producing light energy produces light at a wavelength between 0.4 microns and 2.2 microns.

22. The system as recited in claim 21 in which the means for producing light energy is a laser.

23. The system as recited in claim 3 in which the means for generating the laser beam includes a crystalline laser medium containing ions selected from the group consisting of Holmium$^{+3}$ ions, Erbium$^{+3}$ ions, Thullium$^{+3}$ ions and mixtures thereof.

24. The system as recited in claim 23 in which the laser medium is pumped by a diode laser.

25. A system for changing the shape of the cornea of an eye by heating a corneal stroma to correct vision, the combination comprising:
  means for generating a laser beam which has a wavelength such that the laser beam's absorption coefficient when passing through water ranges from 5 cm$^{-1}$ to 114 cm$^{-1}$;
  means for directing the laser beam onto the cornea, said means being a probe assembly which connects to receive the laser beam and which engages the cornea of a patient;
  means for shaping the laser beam into a treatment pattern to produce a treatment disc which impinges on the central region of the cornea and which causes the central region to flatten such that its focal power is reduced;
  means for controlling the amount of heating in the corneal stroma in a manner such that said laser beam having said wavelength with said absorption coefficient and shaped into said treatment pattern is directed onto the cornea for a period of time of about one second or more delivering laser energy to the cornea at an average energy density throughout the treatment pattern of 0.1 to 1.5 Joules/mm$^2$ to thereby control the change in shape of the cornea without incising, coagulating, scarring or ablating the corneal stroma;
  means for producing light energy;
  means connected to the probe assembly for directing the light energy to the cornea and gathering light energy which is scattered by corneal haze; and
  detector means connected to receive the gathered light energy and being operable to produce a signal indicative of the amount of heating in the corneal stroma.

26. The system as recited in claim 25 wherein said laser beam is directed onto the cornea along the visual axis of the eye.

27. The system as recited in claim 25 in which the diameter of the treatment disc is from 2.0 millimeters to 7.0 millimeters.

28. The system as recited in claim 25 which includes means for contouring the energy density of the treatment disc such that the energy density decreases as a function of radial distance inward from a maximum value near the periphery of the disc.

29. The system as recited in claim 25 in which the means for shaping the laser beam into a treatment pattern produces a pattern having 2 fold rotational symmetry about the center region of the cornea and which causes the cornea to change shape in such manner as to correct astigmatism.

30. The system as recited in claim 25 in which the means for producing light energy produces light at two separate wavelengths and the detector means produces the signal indicative of the amount of heating by comparing the relative amounts of gathered light energy at the two separate wavelengths.

31. The system as recited in claim 25 in which the means for generating the laser beam includes a diode laser.

32. The system as recited in claim 25 in which said laser beam has a wavelength in the range of 1.38 microns to 2.70 microns.

33. The system as recited in claim 25 in which said absorption coefficient of said laser beam when passing through water ranges from 5 cm$^{-1}$ to 45 cm$^{-1}$.

34. The system as recited in claim 25 in which said laser energy is delivered to the cornea in multiple treatments over short time intervals.

35. The system as recited in claim 25 in which said laser energy is delivered to the cornea continuously.

36. The system as recited in claim 25 in which said laser energy is delivered to the cornea by pulsing or modulating the energy input.

37. The system as recited in claim 25 in which the means for shaping the laser beam into a treatment pattern produces at least one line which is directed radially outward from the center of the cornea and the treatment pattern is a series of such radial lines which are disposed around an untreated central region and which cause the untreated central region to flatten such that its focal power is reduced.

38. The system as recited in claim 37 in which the diameter of the untreated central region is from 2.5 to 6.0 millimeters and each radial treatment line has a length of 2.0 to 4.0 millimeters.

39. The system as recited in claim 37 in which the treatment pattern includes from four to eight radial treatment lines which are spaced equidistantly about the untreated central region.

40. The system as recited in claim 25 in which the means for shaping the laser beam into a treatment pattern produces an annular pattern which encircles the central region of the cornea and which causes the curvature of the central region of the cornea to increase such that its focal power is increased.

41. The system as recited in claim 40 in which the outer diameter of the annular treatment pattern is from 4.5 to 9.0 millimeters.

42. The system as recited in claim 25 in which the means for generating the laser beam includes a laser medium containing $Co^{+2}$ ions in an $M_gF_2$ crystalline media.

43. The system as recited in claim 42 in which the laser medium is pumped by a diode laser.

44. The system as recited in claim 25 in which the means for producing light energy produces light at a wavelength between 0.4 microns and 2.2 microns.

45. The system as recited in claim 44 in which the means for producing light energy is a laser.

46. The system as recited in claim 25 which includes an optical fiber having one end positioned in the laser beam and its other end connected to the probe assembly, and the longitudinal axis of the optical fiber at its one end if tilted with respect to the direction of the laser beam.

47. The system as recited in claim 46 which includes means for controlling the amount of tilt to thereby enable the treatment pattern energy density to be controllably contoured.

48. The system as recited in claim 25 in which the means for generating the laser beam includes a crystalline laser medium containing ions selected from the group consisting of Holmium$^{+3}$ ions, Erbium$^{+3}$ ions, Thullium$^{+3}$ ions and mixtures thereof.

49. The system as recited in claim 48 in which the laser medium is pumped by a diode laser.

* * * * *